(12) United States Patent
Kim et al.

(10) Patent No.: US 9,750,951 B2
(45) Date of Patent: Sep. 5, 2017

(54) LIQUID TYPE PLASMA FOR PREVENTING OR TREATING CANCER

(71) Applicant: AJOU UNIVERSITY INDUSTRY-ACADEMIC COOPERATION FOUNDATION, Suwon-si (KR)

(72) Inventors: Chul Ho Kim, Seoul (KR); Sun Yong Kim, Suwon-si (KR)

(73) Assignee: Ajou University Industry-Academic Cooperation Foundation, Suwon-si (KR)

( * ) Notice: Subject to any disclaimer, the term of this patent is extended or adjusted under 35 U.S.C. 154(b) by 0 days.

(21) Appl. No.: 14/982,948

(22) Filed: Dec. 29, 2015

(65) Prior Publication Data

US 2016/0296763 A1    Oct. 13, 2016

(30) Foreign Application Priority Data

Apr. 9, 2015  (KR) .................... 10-2015-0050387
Nov. 3, 2015  (KR) .................... 10-2015-0153582

(51) Int. Cl.
| | | |
|---|---|---|
| *A61N 1/00* | (2006.01) | |
| *A61N 1/44* | (2006.01) | |
| *A61K 33/00* | (2006.01) | |
| *H05H 1/24* | (2006.01) | |

(52) U.S. Cl.
CPC ............. *A61N 1/44* (2013.01); *A61K 33/00* (2013.01); *H05H 1/24* (2013.01); *H05H 2240/20* (2013.01); *H05H 2245/122* (2013.01)

(58) Field of Classification Search
CPC . A61N 1/44; A61K 33/00; H05H 1/24; H05H 2240/20; H05H 2245/122
See application file for complete search history.

(56) References Cited

U.S. PATENT DOCUMENTS

2012/0094250 A1*  4/2012  Lloyd ................ A61C 19/06
                                                        433/80

FOREIGN PATENT DOCUMENTS

KR    1020140003832    2/2016

OTHER PUBLICATIONS

Lee, Sei Young et al. Nonthermal Plasma Induces Apoptosis in ATC Cells: Involvement of JNK and p38 MAPK-Dependent ROS, journal, Nov. 2014,1640-1647, 55(6), Yonsei Medical Journal, Republic of Korea.

(Continued)

*Primary Examiner* — Robert N Wieland
(74) *Attorney, Agent, or Firm* — Weisun Rao; Greenberg Traurig, LLP

(57) ABSTRACT

The present invention relates to a method for preparing a plasma for preventing or treating a cancer. Also, the present invention relates to a liquid type plasma for preventing or treating a cancer prepared by treating the plasma and a pharmaceutical composition for preventing or treating a cancer comprising the same. The plasma and the liquid type plasma according to the present invention can effectively induce cancer cell death without a surgical operation or in a treatment process after a surgical operation, thereby being useful as a novel therapeutic agent and method for a cancer.

5 Claims, 18 Drawing Sheets

(56) References Cited

OTHER PUBLICATIONS

Chang, Jae Won et al. Non-Thermal Atmospheric Pressure Plasma Inhibits Thyroid Papillary Cancer Cell Invasion via Cytoskeletal Modulation, Altered MMP-2/-9/uPA Activity, journal, Mar. 2014, 1-12, 9(3), PLOS One.

Kim, Sun Yong et al. Investigating the Anti-Cancer Effects of Non-Thermal Plasma Through AKT Ubiquitination and Degradation in Head & Neck Cancer, poster, Oct. 25, 2014.

Kang, Su et al. Nonthermal plasma induces head and neck cancer cell death: the potential involvement of mitogen-activated protein kinase-dependent mitochondrial reactive oxygen species, journal, Feb. 13, 2014, 5(1056), Cell Death and Disease.

* cited by examiner

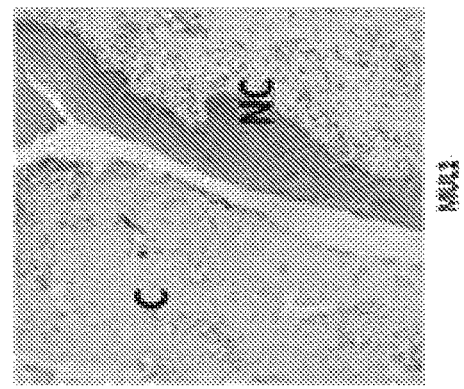
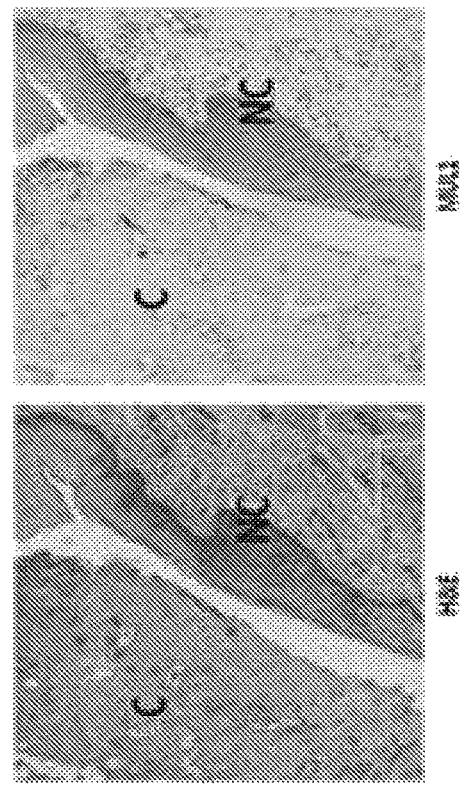
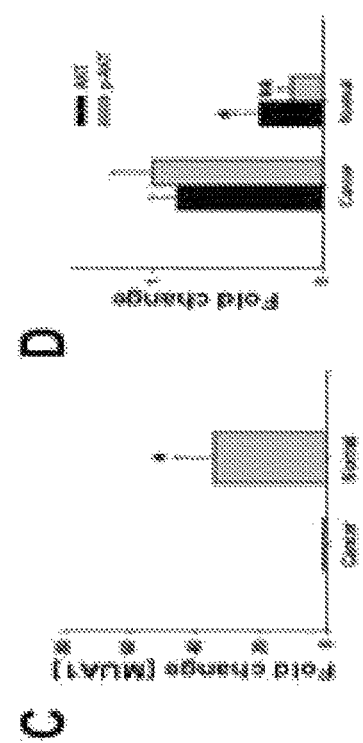
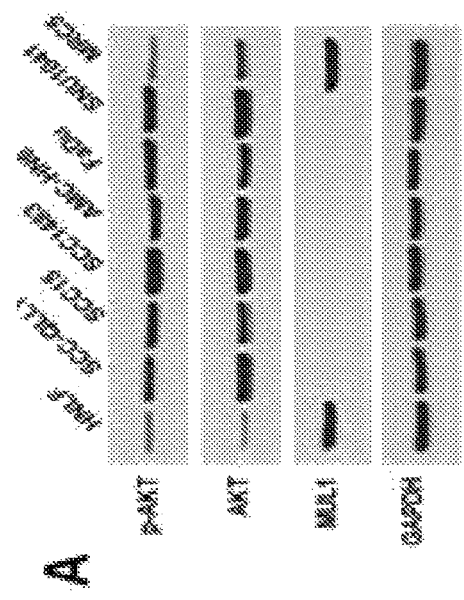
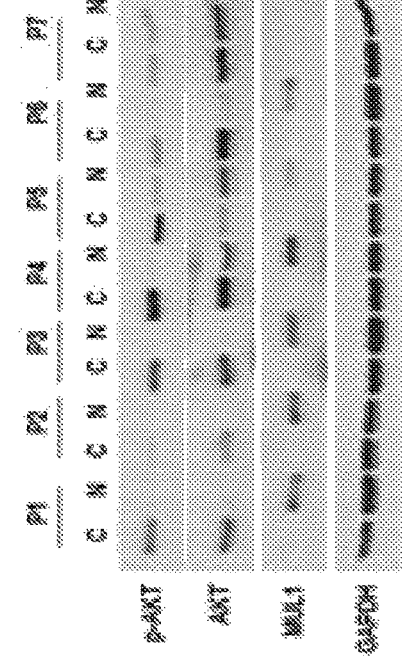
FIG. 7A
FIG. 7B
FIG. 7C
FIG. 7D
FIG. 7E

LIQUID TYPE PLASMA FOR PREVENTING OR TREATING CANCER

CROSS-REFERENCE TO RELATED APPLICATIONS

This application claims priority to Korean Patent Application No. 10-2015-0050387, filed on Apr. 9, 2015, and Korean Patent Application No. 10-2015-0153582, filed on Nov. 3, 2015, the contents of both of which are incorporated herein by reference in their entireties.

TECHNICAL FIELD OF THE INVENTION

The present invention relates to a method for preparing a plasma or a liquid type plasma for preventing or treating a cancer, a liquid type plasma prepared by the method having an effect of preventing and treating a cancer, and a method for treating a cancer using the same.

BACKGROUND OF THE INVENTION

Even nowadays where medical technology has rapidly developed, cancer is a type of disease which has not been completely conquered. Many people are still diagnosed with cancer and die of cancer or complications associated therewith.

Cisplatin is known as a chemotherapy drug very effective in treating a variety of cancers, including lung cancer, breast cancer, bladder cancer, stomach cancer, cervical cancer, or myelomatosis. Cisplatin, which is a heavy metal compound containing a central atom of platinum surrounded by two chlorine atoms and two ammonia molecules in the cis-position, forms an interstrand crosslink between two adjacent guanines on DNA strands, to inhibit DNA synthesis. Cisplatin is attached to a double-strand DNA structure which is present in nuclei of cancer cells, to inhibit DNA replication, suppress the growth and proliferation of cancer cells, and eliminate cancer cells, thereby having an anticancer effect. However, cisplatin resistance causes clinical problems in the treatment of cancers. Therefore, demands for a novel anticancer agent and cancer treatment method, which can replace cisplatin, are on the rise.

Particularly, head and neck cancer, which starts in tissue, such as nasal cavity, pharynx, larynx, salivary gland, thyroid, or the like, accounts for about 5% of malignancies in incidence worldwide. The incidence of head and neck cancer gradually increases worldwide, and for the treatment of head and neck cancer, cisplatin, which is the strongest anticancer agent among anticancer agents currently used in clinical practice, is used. Accordingly, a novel anticancer agent that can replace cisplatin is highly required.

Also, in the case of cancers, a process for eliminating tumors through an operation is very complicate and also causes much physical damage on patients.

Thus, there are demands for a novel method for treating a cancer which can simply replace a surgical method and resolve a resistance issue to previous anticancer agents. However, there are not many reports on a novel therapeutic agent and method which can resolve all these issues.

SUMMARY OF THE INVENTION

It is an object of the present invention to provide a method for preparing a plasma for preventing or treating a cancer, as a novel therapeutic agent and method, capable of treating a cancer by overcoming a resistance issue to previous anticancer agents without an operation.

It is another object of the present invention to provide a method for preparing a liquid type plasma facilitating in vivo applications, including irradiating a medium with the plasma prepared by the above method.

It is yet another object of the present invention to provide a liquid type plasma prepared by the above method having an effect of preventing or treating a cancer and a method for treating a cancer using the same.

In order to achieve the above objects, the present invention provides a method for preparing a plasma for preventing or treating a cancer, including 1) filling a plasma generator with a carrier gas; and 2) generating a plasma by supplying a voltage of 0.5 kV to 20 kV to the carrier gas.

Also, the present invention provides a method for preparing a liquid type plasma, including 1) filling a plasma generator with a carrier gas; 2) generating a plasma by supplying a voltage of 0.5 kV to 20 kV to the carrier gas; and 3) irradiating a medium with the generated plasma.

Also, the present invention provides a liquid type plasma prepared by the above preparation method.

Also, the present invention provides a method for treating a cancer, including 1) filling a plasma generator with a carrier gas; 2) generating a plasma by supplying a voltage of 0.5 kV to 20 kV to the carrier gas; 3) obtaining a liquid type plasma by irradiating a medium with the generated plasma; and 4) treating a subject with the liquid type plasma.

The plasma and the liquid type plasma according to the present invention can effectively induce the death of cancer cells without an operation or in a treatment process after an operation, thereby being useful as a novel therapeutic agent and method for a cancer.

BRIEF DESCRIPTIONS OF THE DRAWINGS

Figure 4A:
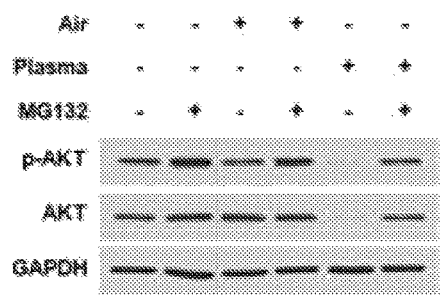
Figure 4C:
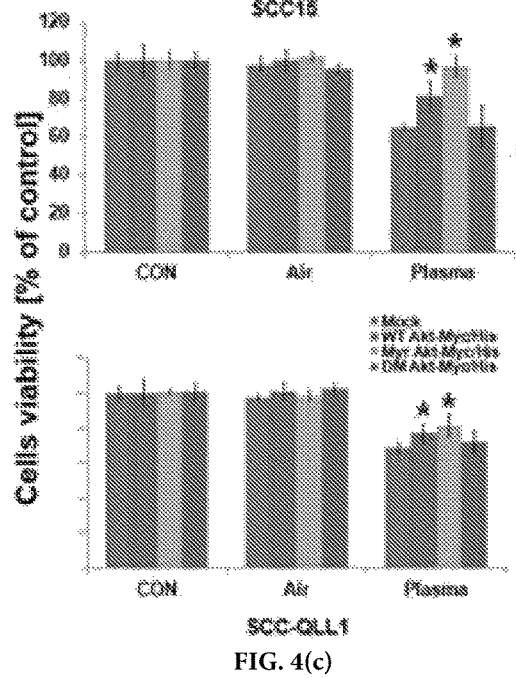
Figure 4B:
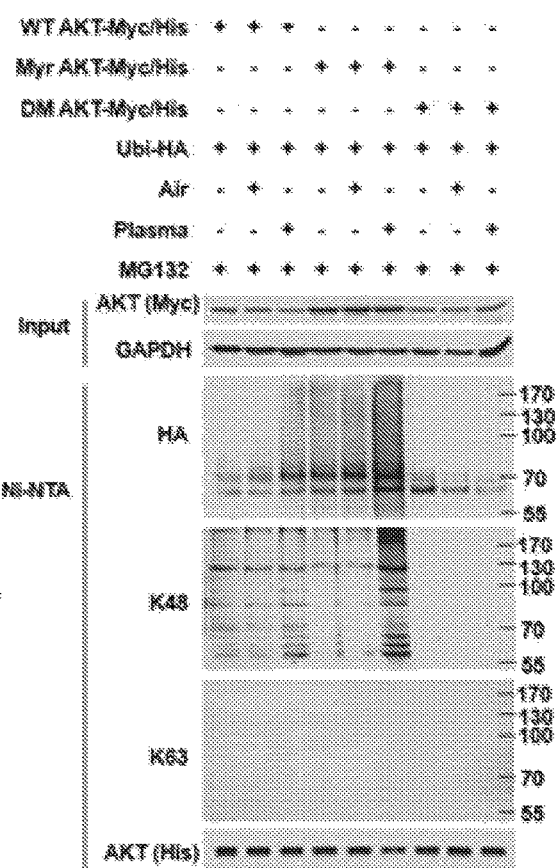

FIG. 4(a) shows a result of confirming inhibition on changes in plasma-induced p-AKT and AKT expressions by MG132 proteasome inhibitor. FIG. 4(b) shows a result of confirming K48-linked ubiquitinated mediation. FIG. 4(c) shows a result of confirming ubiquitinated mediation in plasma-induced cell death.

Figures 5A, 5B:
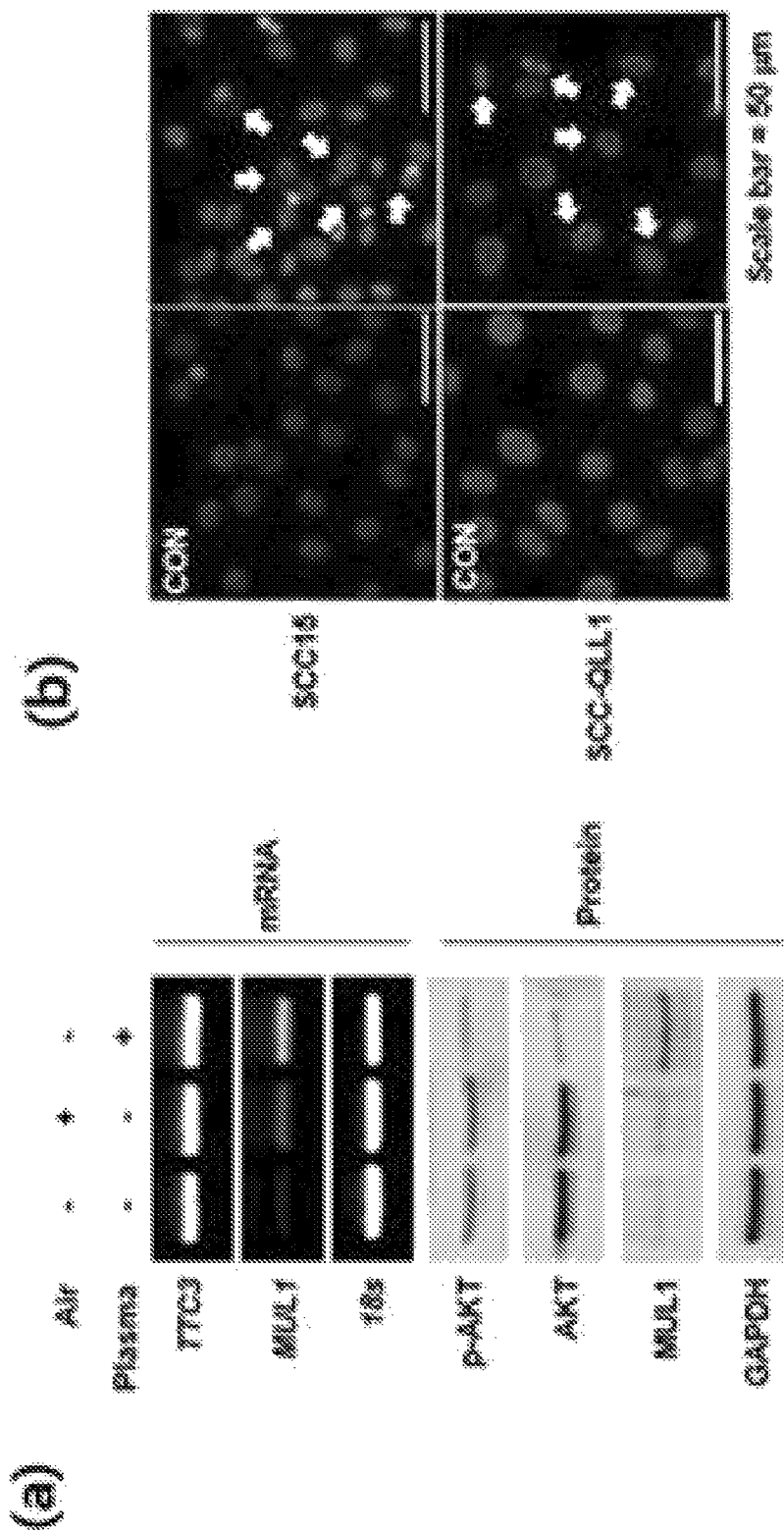

FIG. 5(a) shows a result of confirming an increase in MUL1 expression in HNSCC cells by plasma treatment. FIG. 5(b) shows a result of observing PLA-positive fluorescence.

Figure 6:
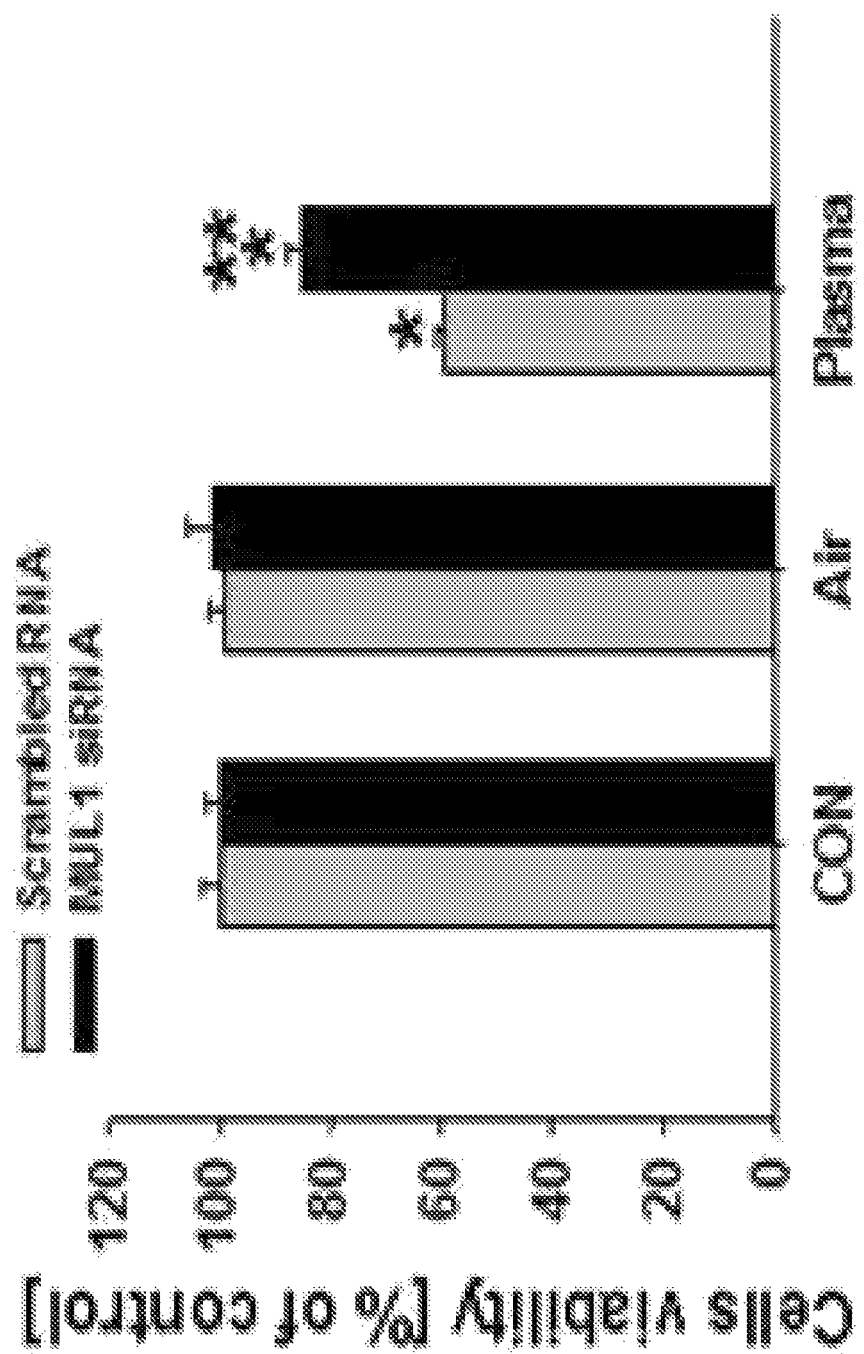

FIG. 6 shows a result of confirming plasma-induced cell death inhibition by MUL1 knockdown, using MUL1 siRNA.

FIGS. 7A and 7B show a result of comparing MUL1 and AKT expressions between normal cells (HNLF and MRC5) and HNSCC cell lines (SCC-QLL1, SCC 15, SCC 1483, AMC-HN6, FaDu, and SNU1041). FIGS. 7C and 7D show a result of quantitatively analyzing MUL1 (FIG. 7C), AKT and p-AKT (FIG. 7D) expressions. FIG. 7E shows a result of confirming a difference in MUL1 expression, through immunohistochemistry analysis. (C: cancer, NC: normal cells)

Figure 8:
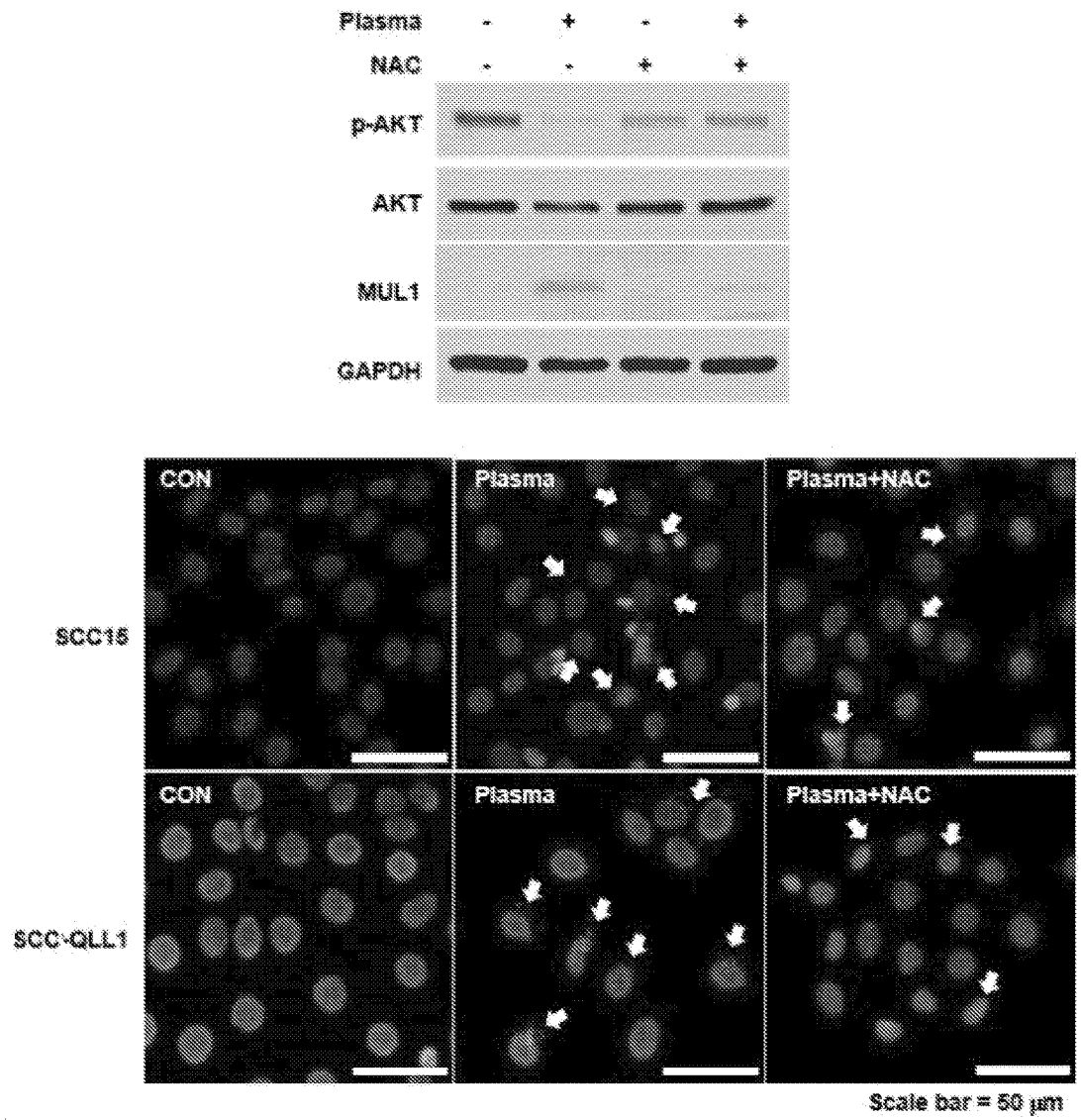

FIG. 8 shows a result of confirming an increase in PLA positive signals by plasma treatment and a decrease in positive signals by plasma+NAC treatment, in SCC15 and SCC-QLL1.

Figure 9:
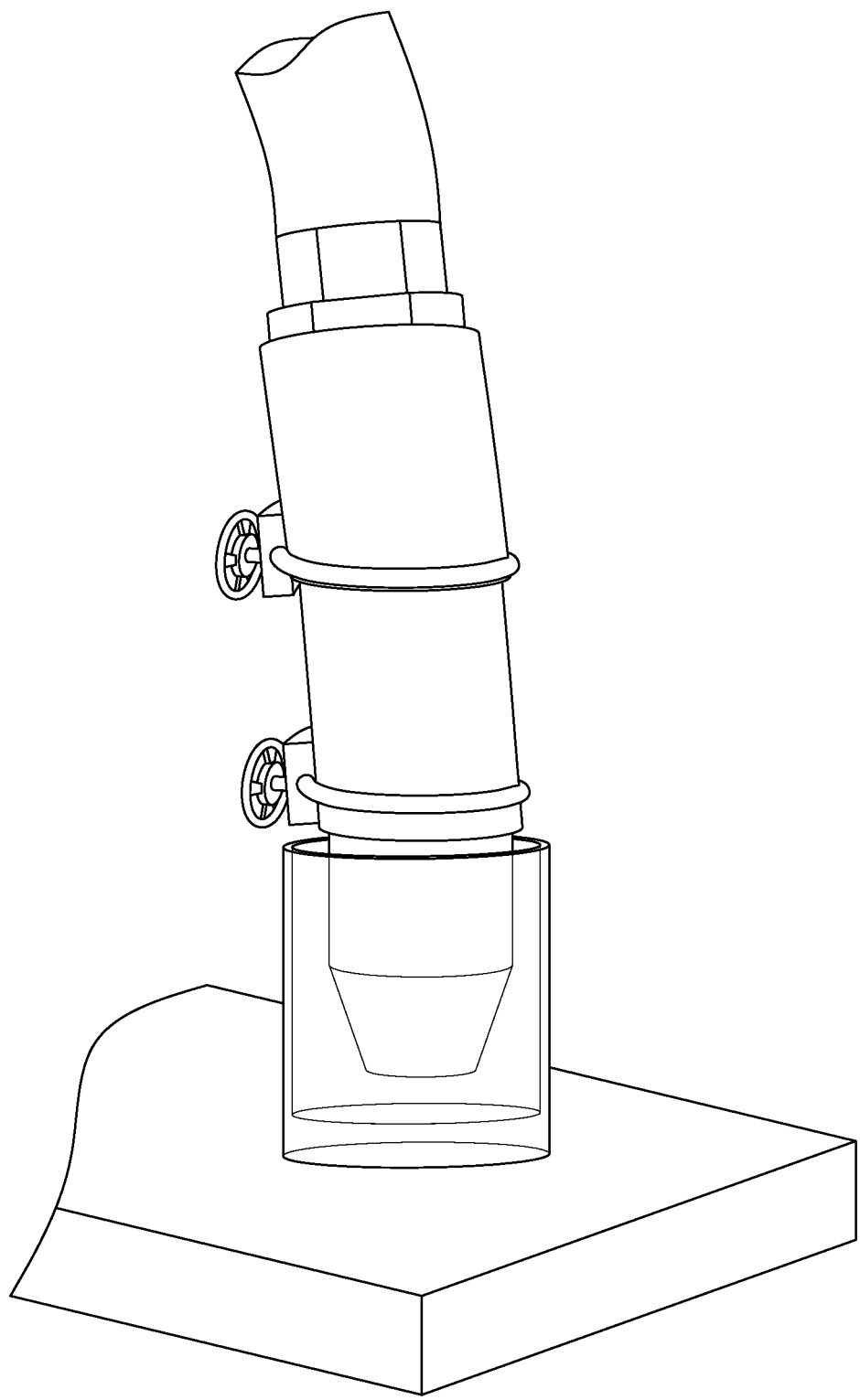

FIG. 9 shows a preparation of a liquid type plasma (LIP).

Figure 10:
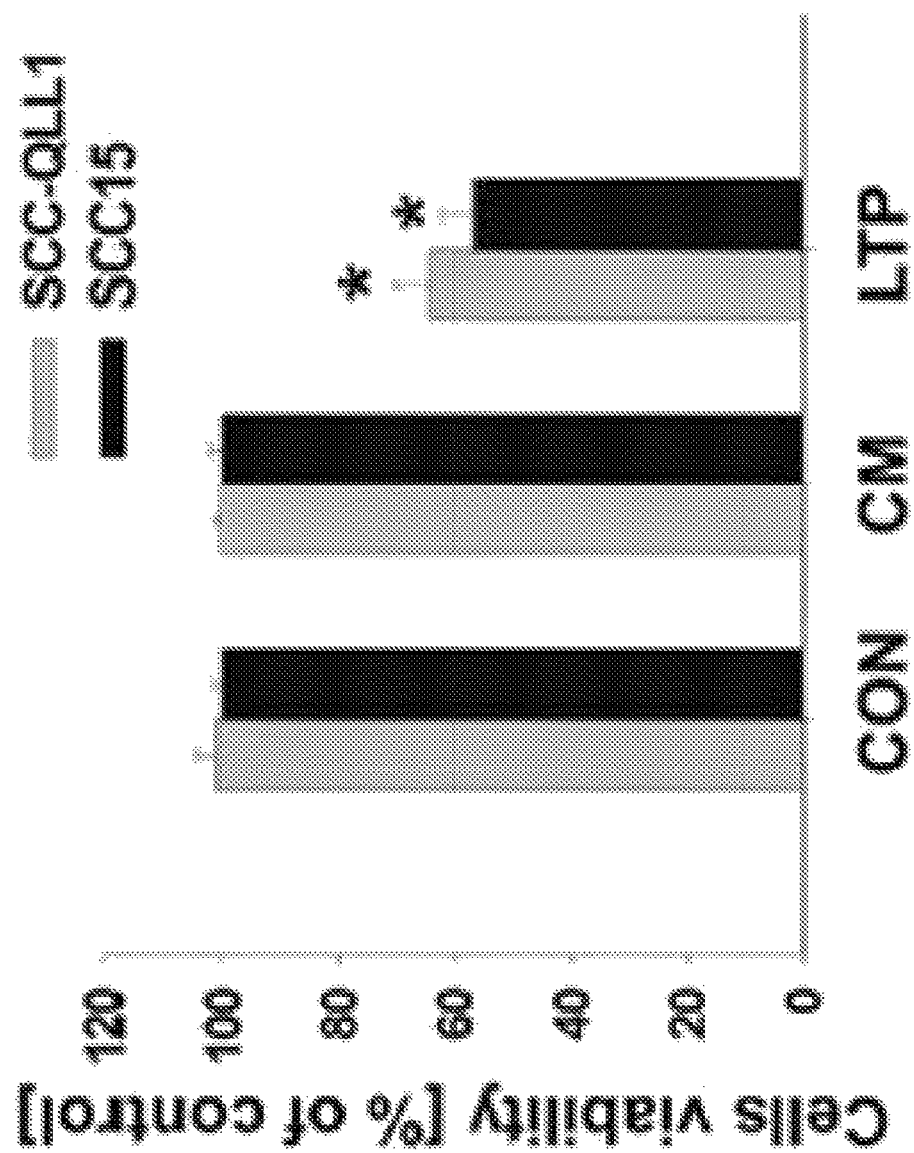

FIG. 10 shows a result of confirming SCC 15 and SCC-QLL1 cells death by LIP treatment (*: p<0.05). (Con: un-treated control group, CM: air-treated media group, LIP: liquid type plasma-treated group)

Figure 11:
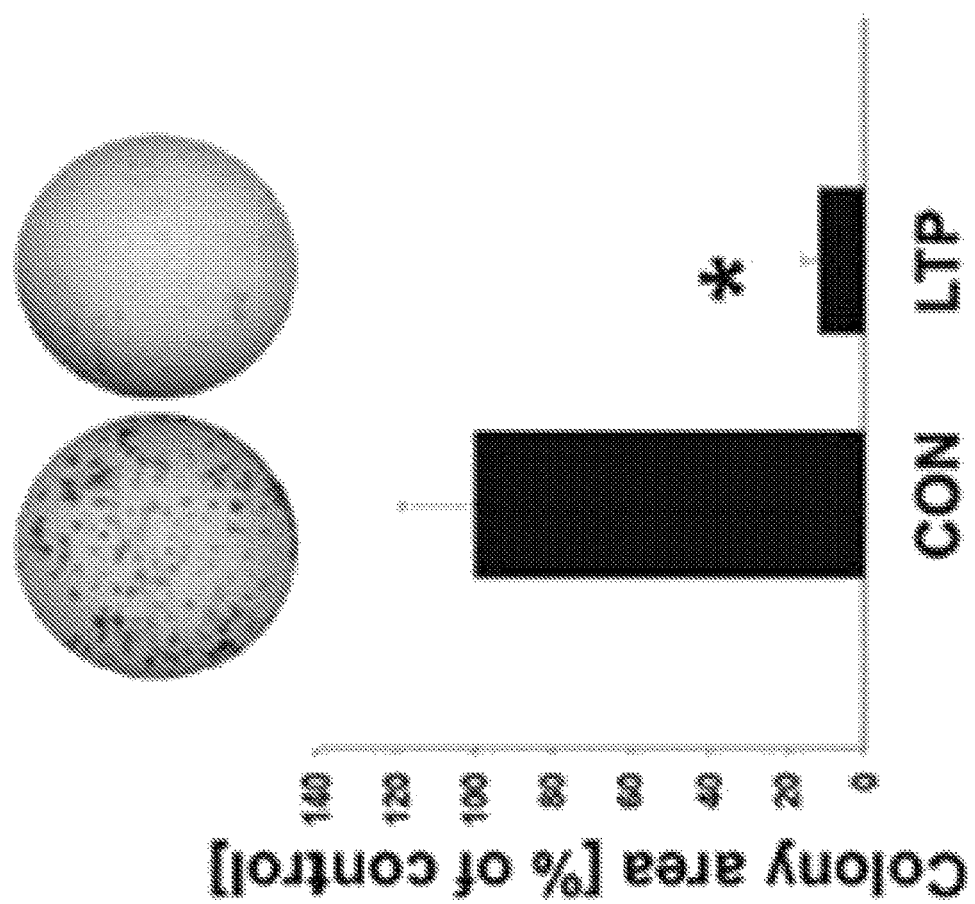

FIG. 11 shows a result of confirming colony-forming inhibition by LIP treatment (*: p<0.05).

Figure 12:
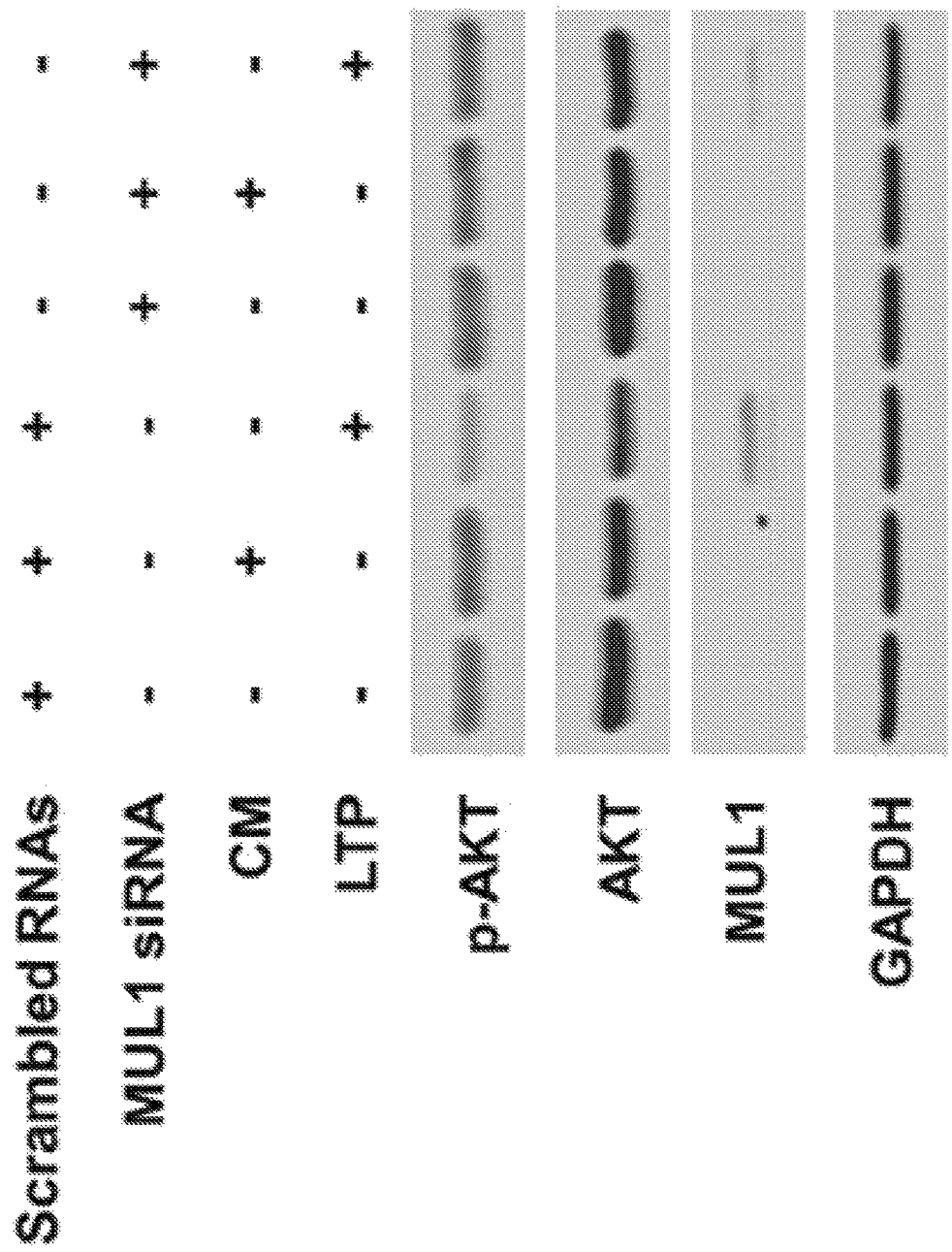

FIG. 12 shows a result of confirming changes in AKT, p-AKT, and MUL1 expressions induced by LIP and inhibition of induction by MUL1 siRNA, through Western blot.

Figure 13:
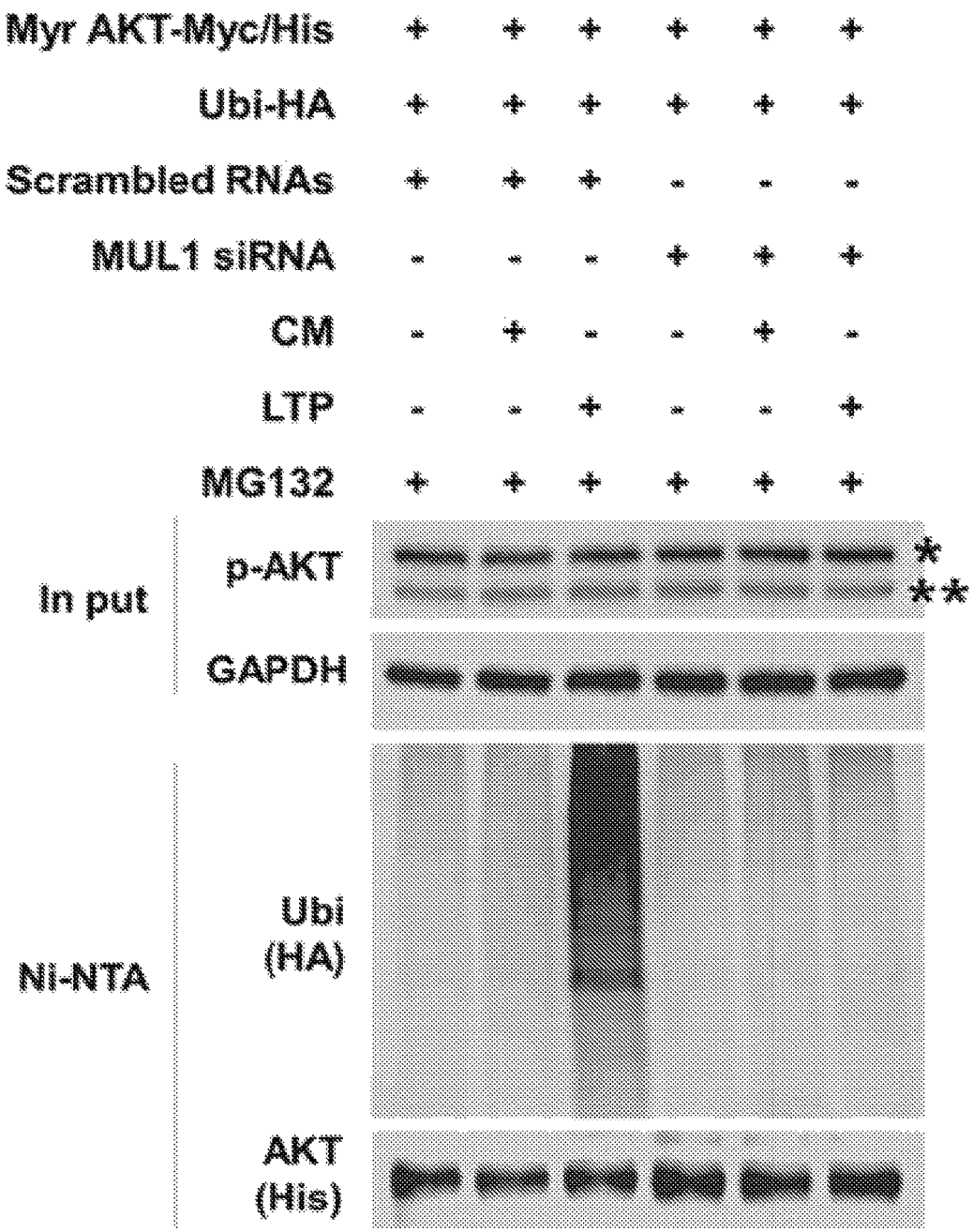

FIG. 13 shows a result of confirming MUL1-mediated AKT ubiquitination induced by LIP treatment.

Figure 14:
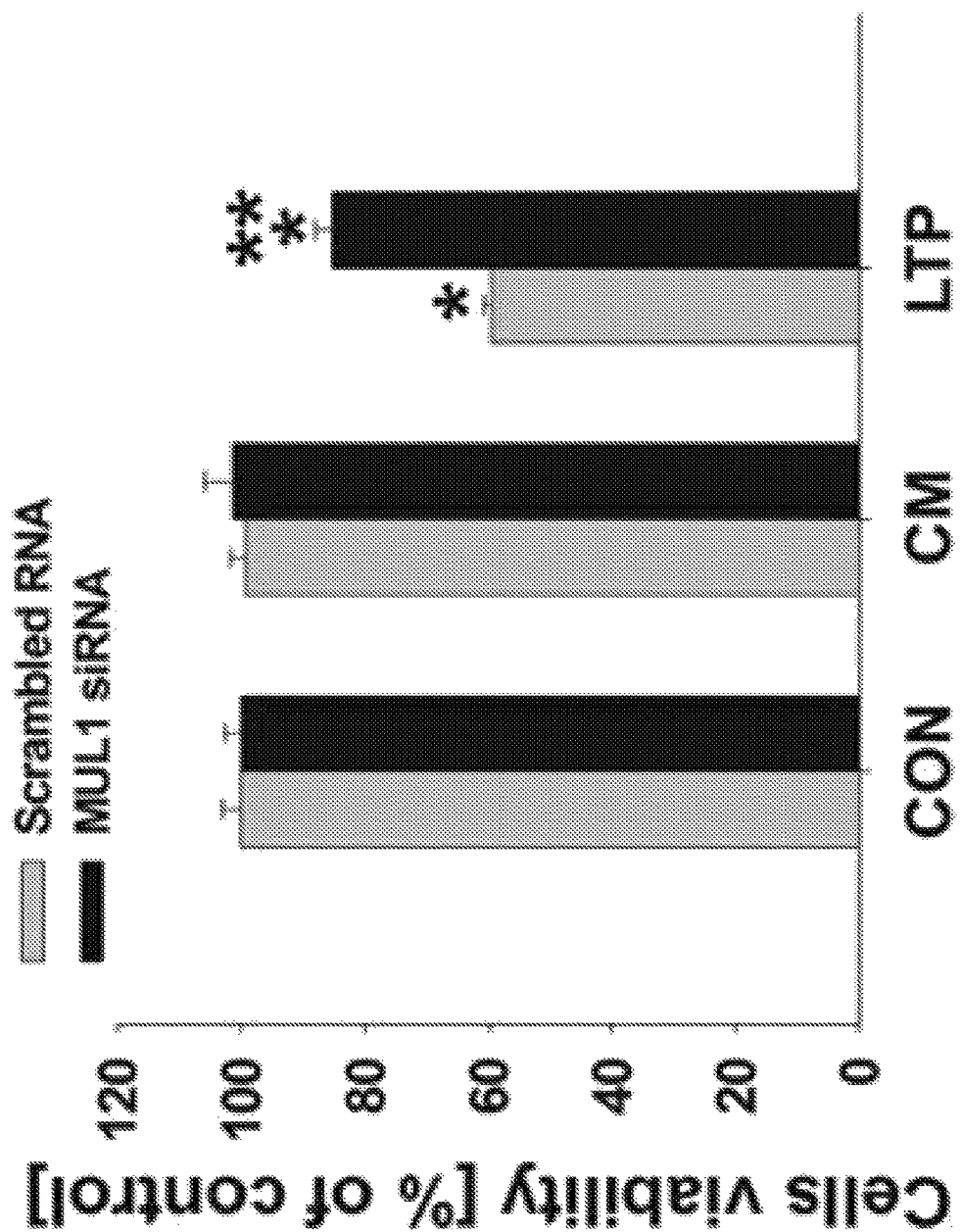

FIG. 14 shows a result of confirming cytotoxicity induced by LIP treatment and cytotoxicity inhibition by MUL1 siRNA, in SCC15 cells (* vs CON; ** vs scrambled RNA).

Figure 15C:
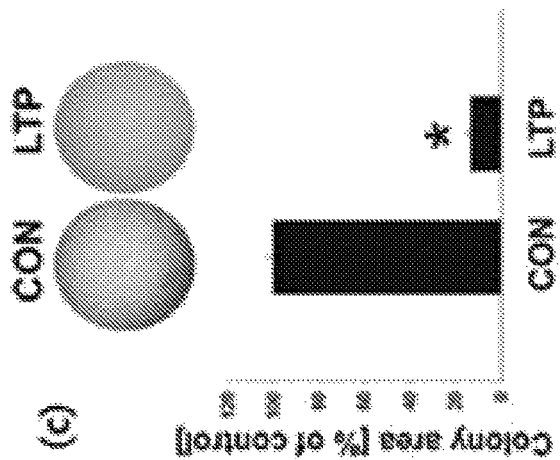
Figure 15B:
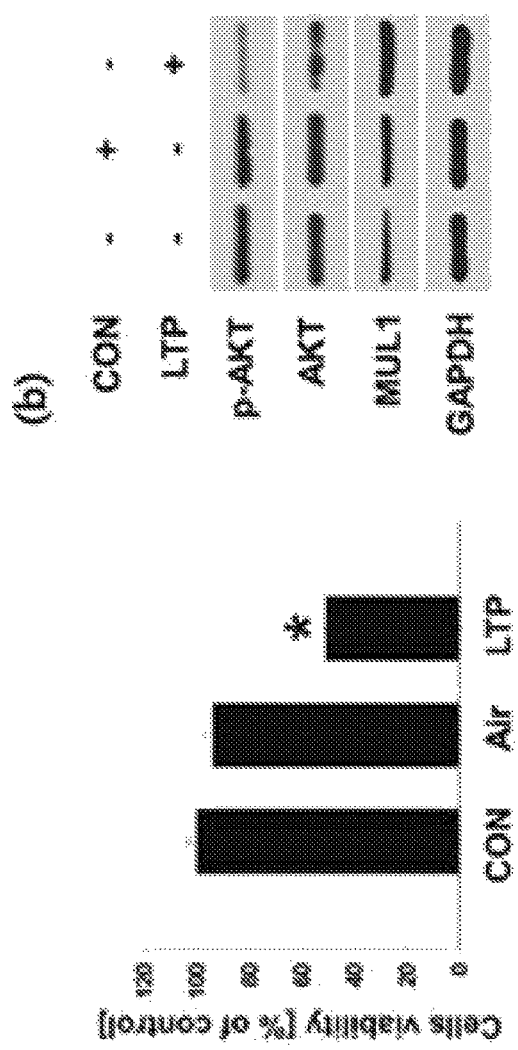
Figure 15A:

FIG. 15(a) shows a result of confirming a change in SCC7 cell viability in syngeneic mouse models by LIP treatment, through an MTT assay. FIG. 15(b) shows a result of confirming changes in p-AKT, AKT, and MUL1 expressions, through Western blot. FIG. 15(c) shows a result of confirming colony-forming ability through crystal violet staining (p<0.05).

Figure 16:
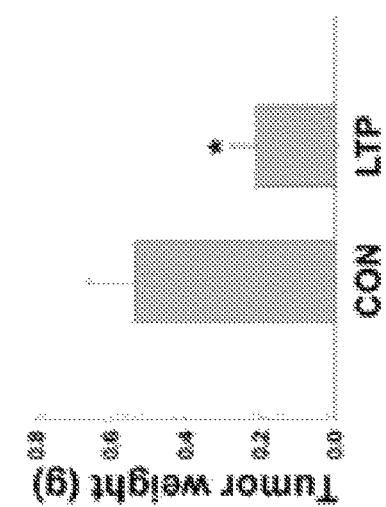
Figure 16:
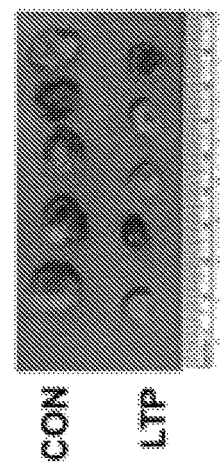
Figure 16:
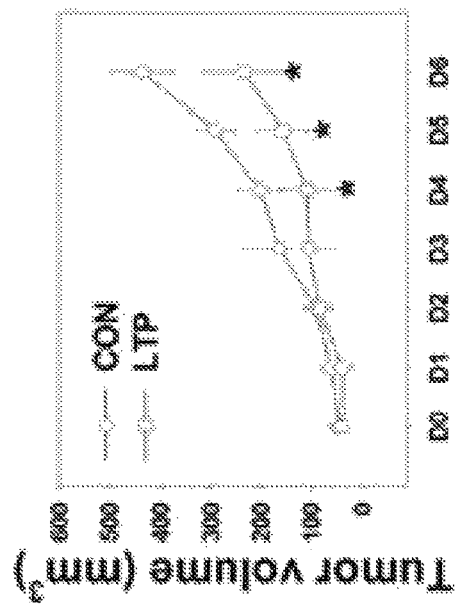

FIG. 16 shows a result of confirming tumor volume, size, and weight of C3H/HeJ mice inoculated with SCC7 cells and treated with LIP.

Figure 17:
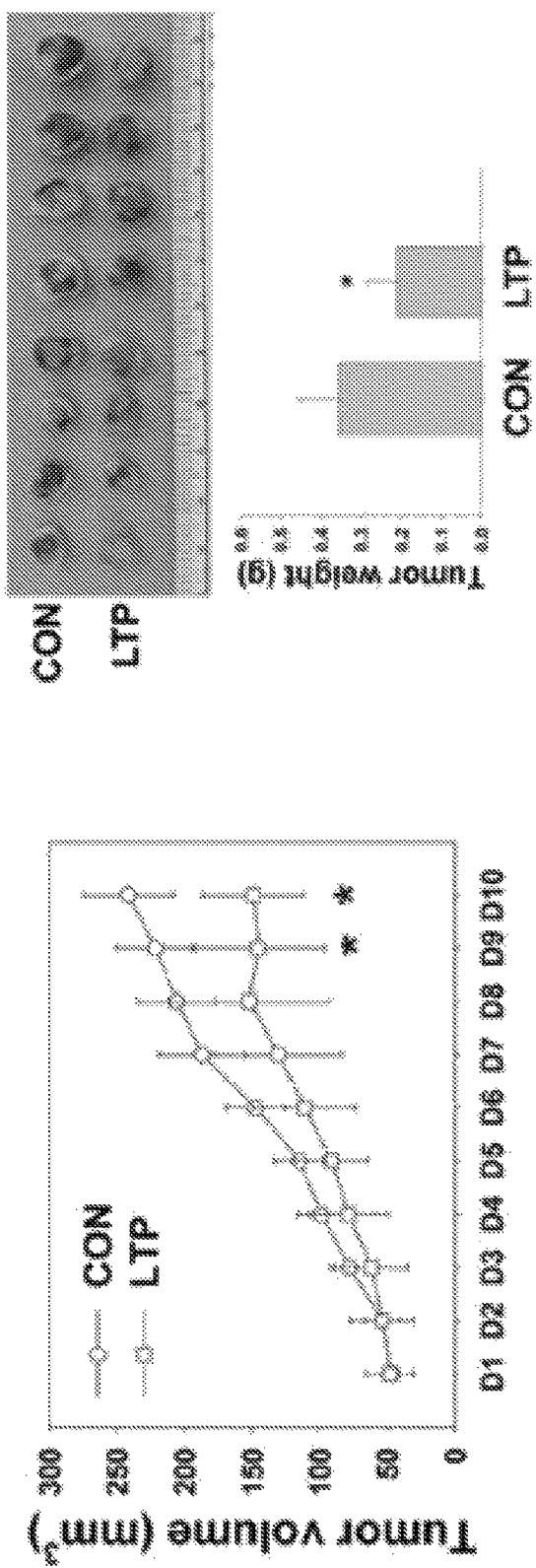

FIG. 17 shows a result of comparing tumor volume, size, and weight by LIP treatment in xenograft in vivo mouse models obtained by administering SCC15 cells to BALB/c nu/nu mice (p<0.05).

Figure 18:
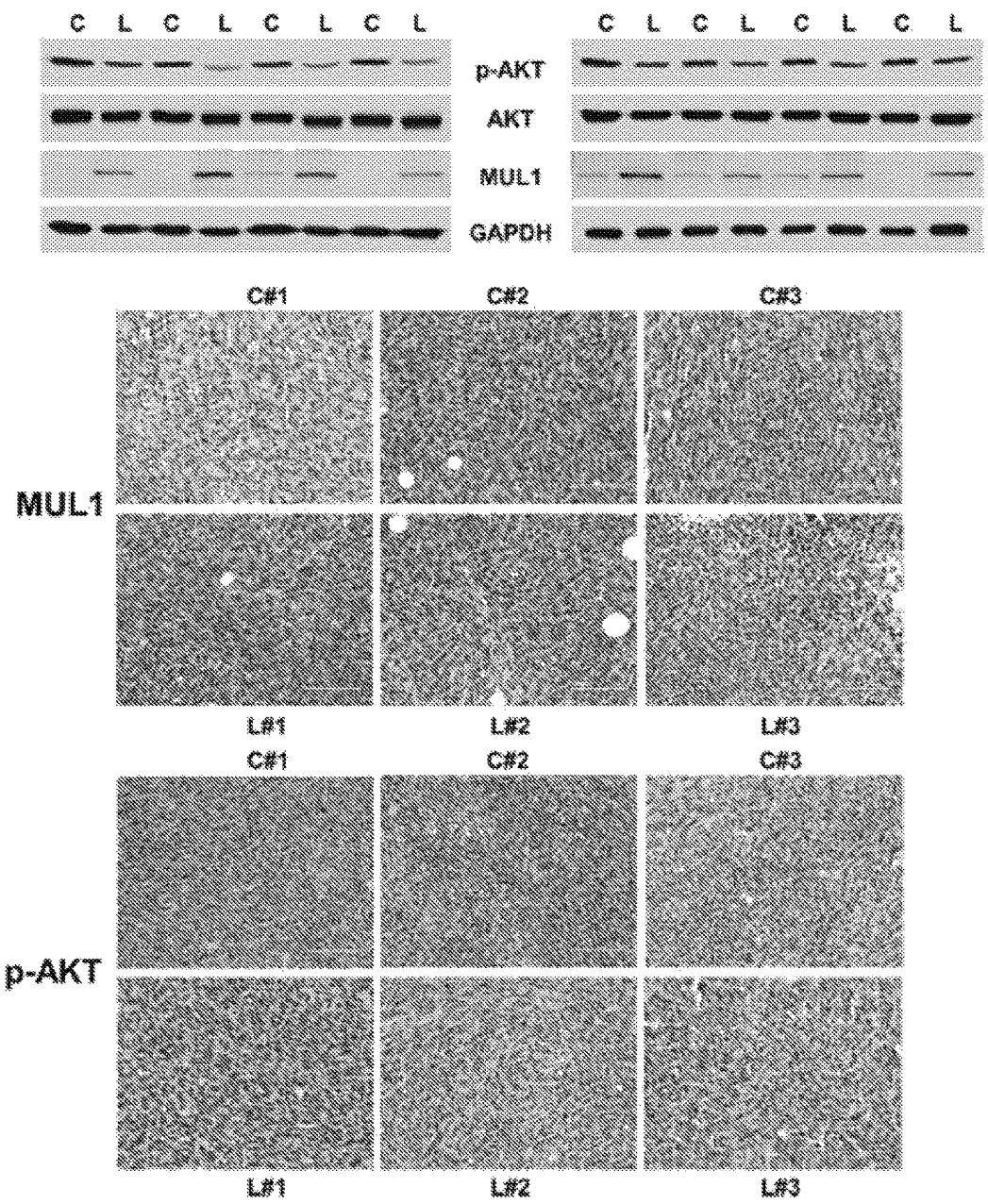

FIG. 18 shows a result of confirming changes in p-AKT, AKT, and MUL1 expressions by LIP treatment in xenograft in vivo mouse models through Western blot and immunohistochemistry analysis (C: control group, L: LIP-treated group).

DETAILED DESCRIPTION OF THE INVENTION

The present invention provides a method for preparing a plasma for preventing or treating a cancer, including 1) filling a plasma generator with a carrier gas; and 2) generating a plasma by supplying a voltage of 0.5 kV to 20 kV to the carrier gas.

The term "plasma" refers to an ionized gas satisfying Debye shielding. Plasma is considered as one of the four fundamental states of a substance, the others being gas, liquid, and solid. With regard to the plasma of the present invention, a neutral gas is phase-transited to a plasma by an external voltage, the excitation and ionization of the neutral gas generate electrons and positive ions, and radicals to which molecular gas is excited may be present.

As the plasma generator, any known plasma generator may be used unlimitedly, as long as it can generate a liquid type plasma that can achieve the objects of the present invention. Particularly, in order to generate a plasma for biological applications, the plasma generator prevents arc and static electricity. For example, the plasma generator according to the present invention may include a main body; a flat ground electrode provided at one side in the main body; a needle or rod power electrode arranged in the main body to be opposite the flat ground electrode; and a high voltage power supply device for supplying electric power to the power electrode.

Particularly, the plasma generator according to the present invention preferably uses a molecular gas as a carrier gas, and may have an arc-free and antistatic polarizing plate and include a pair of electrodes made of Al2O3.

A high tension current supplied to the plasma generator of the present invention may be supplied by a power supplying part supplying power with a voltage of 0.5 kW to 20 kV, 1 kW to 15 kV, and 2 kW minimum to 13 kV maximum, and a mean frequency of 5 to 200 kHZ, 10 to 100 kHZ, and 20 to 30 kHZ. Such plasma generator generates an atmospheric pressure non-thermal plasma (NTP) of room temperature.

As the carrier gas, any carrier gas may be used unlimitedly, as long as it is suitable for preparing a plasma and a liquid type plasma that can achieve the objects of the present invention. However, the carrier gas may be preferably at least one selected from helium, oxygen, and a combination thereof, and a plasma may be generated by supplying a high tension current to the gas.

The cancer that the present invention aims to prevent and treat may unlimitedly include any cancer caused by various cancer cells where the cell death is induced, the degradation of AKT and p-AKT is accelerated, and a MUL1 level increases, by applying a plasma and a liquid type plasma. Examples of the cancer may include thyroid cancer, oral cavity cancer, pharynx cancer, liver cancer, lung cancer, melanoma, and head and neck cancer.

Also, the present invention provides a method for preparing a liquid type plasma, including 1) filling a plasma generator with a carrier gas; 2) generating a plasma by supplying a voltage of 0.5 kV to 20 kV to the carrier gas; and 3) irradiating a medium with the generated plasma.

The liquid type plasma may be prepared using the plasma of the present invention. The liquid type plasma (LTP) according to the present invention is prepared by a technique generating a high-energy, high-density plasma in liquid, and is prepared by being exposed to an atmospheric pressure non-thermal plasma (NTP) of room temperature.

The LTP according to the present invention may have the same meaning as a plasma-conditioned medium (PCM).

The PCM has an anticancer effect equivalent/improved/similar to the radiated plasma through the same mechanism, and has advantages of facilitating delivery and application, compared with the LTP.

As the medium irradiated with the plasma for preparing an LTP of the present invention, any known medium may be used unlimitedly. A medium suitable for culturing a cell may be preferably selected according to the type of the cell for culturing.

The atmospheric pressure NTP of room temperature used for preparing the LTP is a plasma generated with preferably a carrier gas selected from helium, oxygen, or a combination thereof, and more preferably a carrier gas of helium and oxygen.

In preparing the LTP of the present invention, the medium may be preferably irradiated with the plasma at a predetermined distance away from the plasma, at a distance of preferably 0.1 to 15 cm, more preferably 1 to 10 cm, and most preferably 1 to 5 cm.

In preparing the LTP, the medium may be irradiated with the plasma for about 5 to 30 minutes, about 10 to 25 minutes, and about 15 to 20 minutes.

Also, the present invention provides an LTP prepared by the above method.

The LIP, which is prepared by conditioning a medium with a plasma, may have the same meaning as the PCM and have an anticancer effect through the same mechanism as the atmospheric pressure NTP of room temperature.

Accordingly, the present invention provides an LTP for preventing or treating a cancer.

Also, the present invention provides a pharmaceutical composition for preventing or treating a cancer including the LIP, and an anticancer agent including the LTP.

A medium conditioned with the plasma, i.e., the LIP, effectively induces the death of cancer cells, such as thyroid cancer, oral cavity cancer, pharynx cancer, liver cancer, lung cancer, melanoma, and head and neck cancer, thereby achieving the object of preventing or treating the cancer.

The composition of the present invention includes a pharmaceutically acceptable carrier. The pharmaceutically acceptable carrier included in the pharmaceutical composition of the present invention, which is generally used in formulating the composition, may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxy benzoate, propylhydroxy benzoate, talc, magnesium stearate, mineral oil, saline solution, phosphate buffered saline (PBS), or a medium, but is not limited thereto.

In addition to the above ingredients, the pharmaceutical composition according to the present invention may further include a lubricant, a humectant, a sweetener, a fragrant, an emulsifying agent, a suspending agent, a preservative, etc. Suitable pharmaceutically acceptable carriers and formulations are described in detail in Remington's Pharmaceutical Sciences.

The pharmaceutical composition according to the present invention may be administered orally or parenterally, preferably parenterally.

An appropriate dosage of the pharmaceutical composition of the present invention may vary depending on a variety of factors including the method of formulation, the mode of administration, the patient's age, weight, and gender, pathological condition, diet, the time of administration, the route of administration, excretion rate, response sensitivity, and the like.

The pharmaceutical composition according to the present invention in combination with primary therapy, for example, cancer treatment by chemical therapy or a surgical operation, may induce faster performance of the primary therapy and reinforce its anticancer performance. Accordingly, the plasma and the LIP according to the present invention may be used for increasing the effect of an anticancer agent in chemical therapy, which is a main therapeutic agent primarily used, and optimizing the effect of cancer treatment by being treated to cancer cells left after the surgical operation.

Also, the present invention provides a method for preventing or treating a cancer, including treating a subject with a plasma for preventing or treating a cancer, including 1) filling a plasma generator with a carrier gas; and 2) generating a plasma by supplying a voltage of 0.5 kV to 20 kV to the carrier gas.

Also, the present invention provides a method for treating a cancer, including 1) filling a plasma generator with a carrier gas; 2) generating a plasma by supplying a voltage of 0.5 kV to 20 kV to the carrier gas; 3) obtaining a liquid type plasma by irradiating a medium with the generated plasma; and 4) treating a subject with the liquid type plasma.

The subject may be mammals including humans, include all patients who require cancer treatment including patients under cancer treatment, patients who have undergone cancer treatment, patients who need to undergo cancer treatment, and also include patients who have undergone a surgical operation of removing a cancer for cancer treatment.

More preferably, the LIP according to the present invention may be treated to patients who have not undergone a cancer operation, as a substitute means for treating the cancer without a cancer operation, or to patients who have undergone a cancer operation for providing better prognosis.

Accordingly, the present invention provides a method for improving the prognosis of a cancer, including 1) filling a plasma generator with a carrier gas; 2) generating a plasma by supplying a voltage of 0.5 kV to 20 kV to the carrier gas; 3) obtaining a liquid type plasma by irradiating a medium with the generated plasma; and 4) treating a subject who has undergone a cancer operation with the liquid type plasma.

In the present invention, the treatment may be interchangeably used with the administration.

Hereinafter, preferred preparation examples and examples are provided for helping better understand the present invention. The following preparation examples and the examples are provided for illustrative purposes only, and those skilled in the art will appreciate that the present invention is not limited to the scope of the preparation examples and the examples.

Example 1. Induction of Cell Death of Head and Neck Cancer by Plasma 1.1 Preparation of Plasma A plasma device was designed and manufactured as a spray-type atmospheric pressure plasma with a newly designed arc-free and antistatic plate to prepare uniform plasma for biological research applications. The plasma device inhibits arc and static electricity, and more specifically, has a plasma source equipped with a pair of electrodes made of Al2O3 (high-voltage and ground electrodes, 10×40 mm2 in dimension, 2 mm gap between electrodes) isolated from a direct contact with the plasma using a ceramic barrier. The specifications of the power supply with this system are 2 kV minimum, 13 kV maximum, and mean frequency 20 to 30 kHz; these specifications can vary in various ranges depending on the type and amount of gas used. To be specific, helium and oxygen were used as a carrier gas. The voltage and current of plasma were measured uniformly and stably. The plasma density using helium and oxygen as a carrier gas was calculated as 106/m3 based on optical emission spectroscopy, and the density of ROS, which is reactive oxygen species, was calculated as 1013/m3. The temperature of plasma gas was kept to be 35° C. or lower after 10 minute treatment at 13 kV for plasma treatment.

The plasma thus prepared was treated to SCC-QLL1 or SCC15 cells, which are head and neck cancer cells originating from human oral cavity cancer, for 24 hours, and the effect thereof was analyzed, in order to confirm that the plasma is effective in treating oral cavity cancer.

1.2 Analysis of Cell Viability

In order to confirm that the above-prepared plasma causes death of head and neck carcinoma originating from oral cavity cancer, SCC-QLL1 or SCC15 cells were seeded on 48-well plates at a density of 150 cells/mm2. Cells were exposed to air (helium and oxygen gas) for a control group and to plasma for an experimental group, for 24 hours in each cell culture medium under the same condition in the absence of serum. After 24 hours, cell viability was examined using an MTT assay. The result is shown in FIG. 1.

Figure 1:
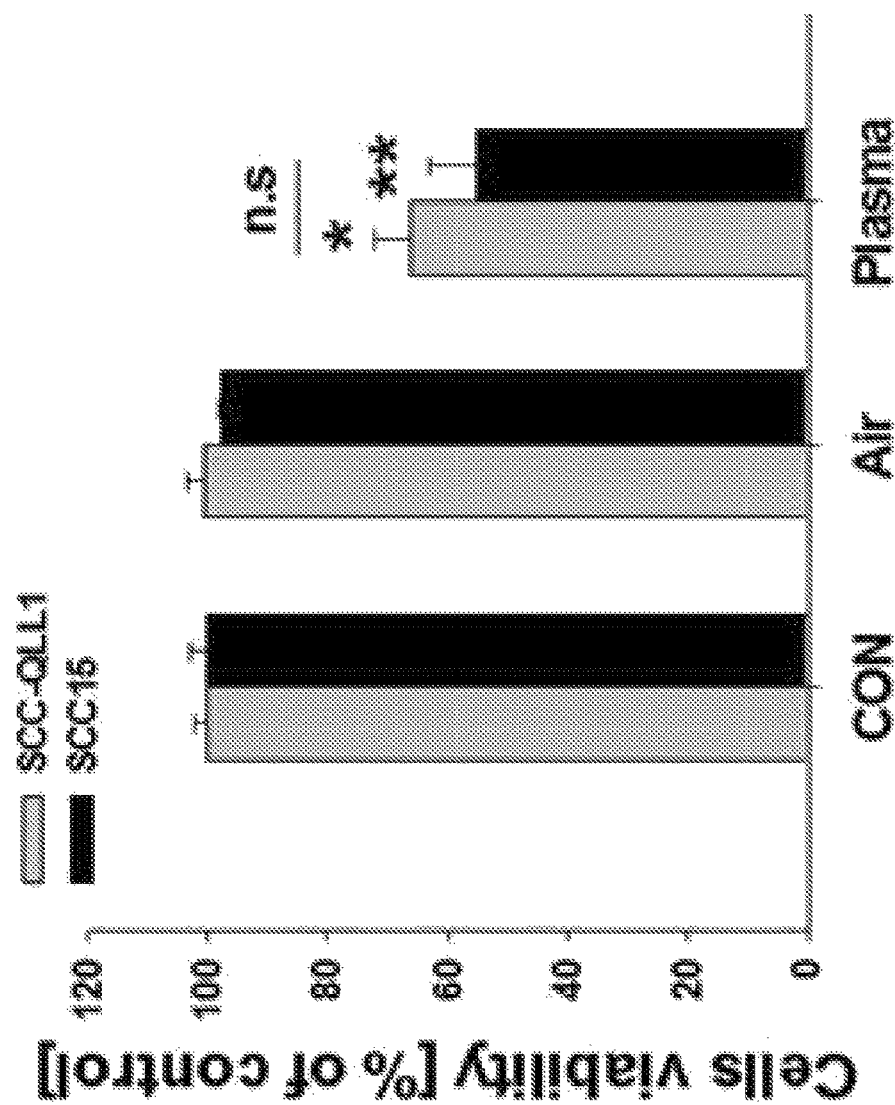
FIG. 1 shows a result of confirming cell viability of oral cavity cells (SCC15 and SCC-QLL1) by plasma treatment, through an MTT assay ($P<0.05$, n=6).

As shown in FIG. 1, the plasma treatment significantly reduced viability of two types of oral cavity cancer cells. Cells cultured in the medium treated with the helium and oxygen gas used as the control showed no change in cell viability, whereas both oral cavity cancer cells, SCC-QLL1 and SCC15, exposed to the plasma showed a significant reduction in cell viability down to about 50 to 60%, as compared with the control. From the result, it was confirmed that plasma can effectively kill cancer cells.

1.3 Change in Cellular AKT Level by Plasma

The AKT kinase is known as playing an important role in cell survival, apoptosis, and head and neck cancer development. As confirmed above, the plasma treatment accelerated cancer cell death. Thus, in order to determine whether the cell death effect induces a change in cellular AKT, p-AKT, AKT, and phosphor-AKT substrate (PAS) expressions were evaluated by Western blot. In order to determine whether AKT and p-AKT degradation is performed by plasma in a time-dependent manner, SCC15 cells were treated with plasma in a serum-free medium for 2 to 24 hours and were observed using Western blot. The result is shown in FIG. 2.

Figures 2A, 2B:
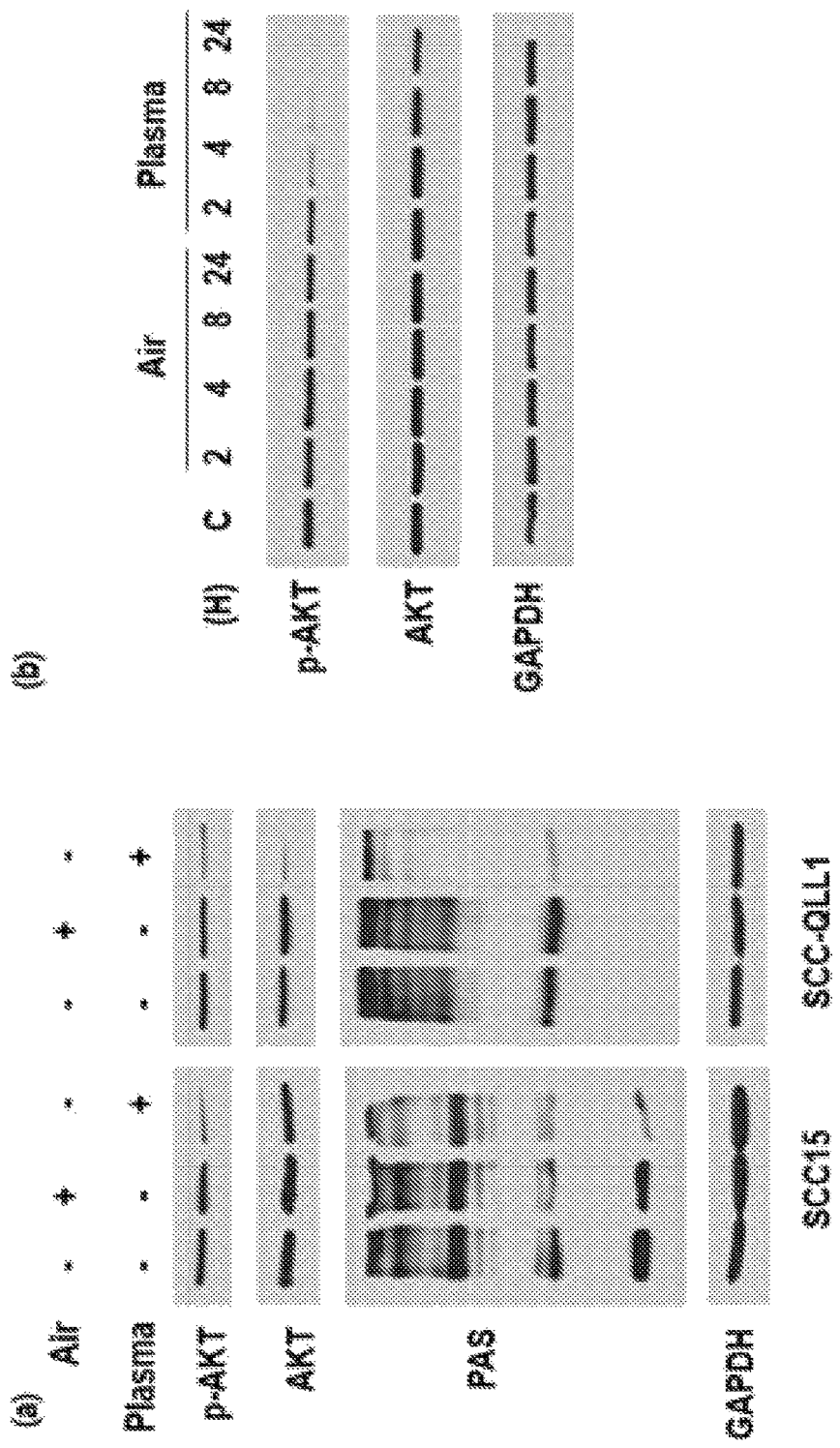
FIG. 2(a) shows a result of confirming changes in p-AKT, total AKT, AKT, and phosphor-AKT substrate (PAS) expressions in plasma-treated oral cavity cancer cells through Western blot.
FIG. 2(b) shows a result of confirming changes in p-AKT and total AKT expressions over the time of liquid type plasma treatment (Air: control group).

As shown in FIG. 2, it was confirmed that for oral cavity cancer cells treated with plasma, both p-AKT and total AKT were reduced and also AKT kinase activity was reduced, as compared with the control. In contrast, for both cancer cells of the control treated with air, neither the amounts of p-AKT and total AKT, nor AKT kinase activity was changed. See FIG. 2(a). Further, it was confirmed that p-AKT and total AKT were gradually reduced in a time-dependent manner over the time of plasma treatment time. See FIG. 2(b). Particularly, the reduction of p-AKT was observed 4 hours after the plasma treatment.

Figure 3:
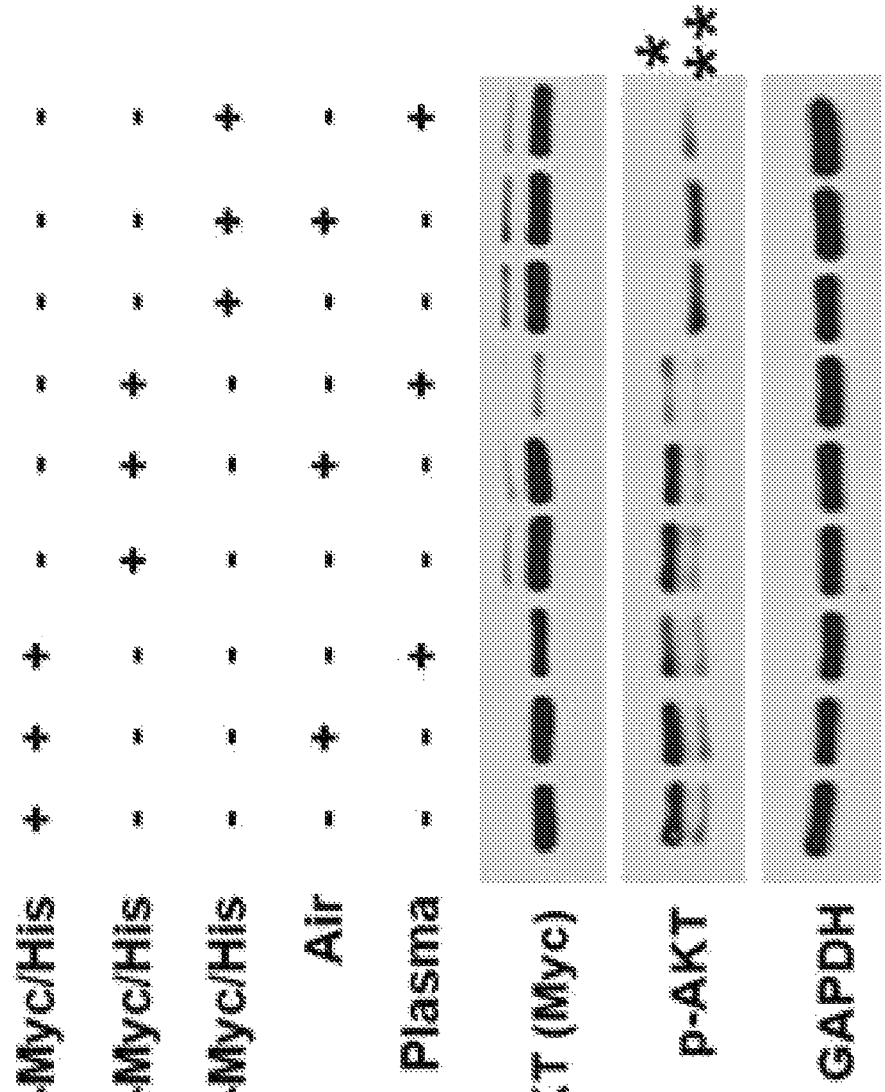
FIG. 3 shows a result of confirming changes in p-AKT and total AKT in SCC15 cells transfected with WT AKT-Myc/His, myristoylated AKT (Myr AKT-Myc/His), and dual mutant AKT plasmid (T308A/S473A dual mutant, DM AKT-Myc/His).

In this regard, to confirm whether plasma further induces the mechanism of reducing p-AKT than inactive form of AKT, several AKT plasmids including constitutively active myristoylated AKT (Myr AKT-Myc/His) or inactive AKT double mutant plasmid (T308A/S473A double mutant, DM AKT-Myc/His) were transfected into SCC15 cells. FIG. 3 shows changes in AKT and p-AKT levels.

As shown in FIG. 3, active AKT (p-AKT) was preferentially degraded by plasma. In the wild-type AKT (WT AKTMyc/His)-transfected cells, the plasma treatment reduced AKT level. However, a much stronger decrease in p-AKT level was observed in the inactive-type AKT-transfected cells upon plasma treatment. Further, as compared with myristoylated AKT-transfected cells, in the inactive-type AKT, AKT level was not changed by plasma. From this result, it was confirmed that plasma can induce cancer cell death by regulating AKT activity through the mechanism of preferentially degrading active AKT in carcinoma originating from oral cavity cancer.

1.4 K48-Linked Ubiquitination by Plasma

Based on the confirmation that plasma induces oral cavity cancer cell death through the AKT degradation pathway, it was examined whether the cell death mechanism is associated with the ubiquitin-dependent proteasomal degradation system (UPS) in SCC 15 cells, which are head and neck squamous cell carcinoma (HNSCC). SCC 15 cells were treated with plasma for 24 hours, and 10 μM of MG132 was added 6 hours before cell harvest. Then, p-AKT and AKT were analyzed. Further, in order to determine whether plasma more preferentially ubiquitinates active AKT, wild-type AKT (WT AKT-Myc/His), active AKT (Myr AKT-Myc/His), and inactive AKT (DM AKT-Myc/His) were transfected into SCC15 cells together with ubiquitin plasmid (Ubi-HA). After 24 hours of transfection, cells were treated with plasma and cultured for 24 hours under serum-free conditions containing 1 mM of MG132. AKT ubiquitination was examined using Ni-NTA pull-down assay and Western blot. Further, it was determined with which K48-linked ubiquitinated protein or K63-linked ubiquitinated protein the plasma-induced AKT ubiquitination is associated, using ubiquitin antibodies. The result is shown in FIG. 4.

As shown in FIG. 4, the plasma treatment induced p-AKT and total AKT degradation, and ubiquitination of wild-type AKT was induced by the plasma treatment. The degradation was inhibited in the presence of MG132, a proteasome inhibitor. None of AKT levels was changed in the control group treated with air. This result indicates that plasma-induced AKT degradation is induced by UPS. See FIG. 4(a). Also, it was demonstrated that AKT degradation was performed via K48-linked ubiquitination. See FIG. 4(b). It was confirmed from the change in cell viability that the mediated AKT ubiquitination caused by the plasma treatment plays a pivotal role in plasma-induced cancer cell death. See FIG. 4(c).

1.5 Plasma-Induced MUL1-Mediated Cell Death

As AKT ubiquitination in HNSCC cells induces K48-linked ubiquitination, it was further examined whether MUL1, an E3 ligase for AKT, is involved in plasma-induced AKT ubiquitination. First, changes in proteins and mRNA of MUL1 or TTC3 in HNSCC cells and those after the plasma treatment were examined through RT-PCT and Western blot. Further, in order to examine the binding between AKT and MUL1, SCC15 or SCC-QLL1 human oral cavity cancer cells were attached on glass cover slips and cultured overnight. On the next day, cells were treated with plasma under serum-free conditions, and MUL-1-AKT binding was observed using PLA. The result is shown in FIG. 5.

As shown in FIG. 5, the amount of TTC3 in HNSCC cells was not changed by the plasma treatment, whereas the MUL1 expression was increased by the plasma treatment, and p-AKT and AKT levels were decreased by the plasma treatment. See FIG. 5(a). This result indicates that AKT degradation induced by the plasma treatment is mediated by MUL1. PLA assays also showed similar protein binding patterns between MUL1 and AKT. No PLA-positive fluorescence was observed in cells not-treated with plasma, as endogenous MUL1 expression is suppressed in oral cavity cancer cells. However, PLA-positive signals were noticeably observed in cells treated with plasma, as the binding between MUL1 and AKT increased by plasma-induced MUL1 expression. See FIG. 5(b).

Further, plasma-induced AKT degradation was reduced by MUL1 siRNA transfection and inhibition of K48-linked ubiquitination suppression. Particularly, as shown in FIG. 6, MUL1 knockdown by MUL1 siRNA prevented plasma-induced cytotoxicity, which results in improvement of cancer cell viability. This result indicates that MUL1 plays a pivotal role in plasma-induced HNSCC cell death.

1.6. Comparison in MUL1, AKT, and p-AKT Expressions in HNSCC

As plasma was confirmed to induce the death of HNSCC cell lines through MUL1-mediated AKT degradation, it was examined whether MUL1 expression is changed in HNSCC cell lines compared with normal cells, such as normal human lung fibroblast (NHLF) or MRC5, and endogenous AKT, p-AKT, and MUL1 expressions were evaluated by Western blot. Three human oral cavity cancer-originated head and neck squamous cell carcinoma cell lines (SCC-QLL1, SCC15, and SCC1483) and human hypopharynx cancer cells (FaDu) were purchased from the American Type Culture Collection (ATCC). SNU 1041 human head and neck cancer cells and human lung fibroblasts were purchased from the Korean Cell Line Bank (KCLB). Floor of mount cancer AMC-HN6 was provided by Asan Medical Center. Human normal lung fibroblast (HNLF) was purchased from Lonza. SCC-QLL1, FaDu, HN6, and MRC5 cells were grown in Minimum Essential Medium (MEM) supplemented with 10% FBS and penicillin-streptomycin at 100µ/mL (GIBCO). SCC15 and SCC1483 cells were maintained in Dulbecco's Modified Eagle's Medium (DMEM) at 37° C. with 5% CO2 under humidified conditions. Particularly, endogenous AKT, p-AKT, and MUL1 expressions in patients suffering from head and neck cancer were identified, and each protein level and MUL1 level were quantified in the tissue of seven head and neck cancer patients and normal tissue. The result is shown in FIG. 7.

As shown in FIG. 7, MUL1 expression was suppressed in all HNSCC cell lines, but was very strong in normal fibroblasts. Consistent with the MUL1 expression pattern, AKT and p-AKT levels were distinguished between normal and HNSCC cells. See FIGS. 7A and 7B. Also, it was shown that MUL1 expression was very distinctively suppressed in the tissue of head and neck cancer patients. See FIG. 7C. On the contrary to MUL1 expression, AKT or p-AKT level was much higher in HNSCC cells than in normal cells. See FIG. 7D.

Based on immunohistochemistry analysis on difference in MUL1 expression, it was confirmed that MUL1 was more strongly stained in a non-cancer area than in a cancer area. This is shown in FIG. 7E. This result indicates that MUL1 expression/regulation is associated with AKT level in head and neck cancer development.

Accordingly, it can be understood that liquid type plasma inducing changes in MUL1, AKT, or p-AKT levels in HNSCC cells eventually induces cancer cell death through changes in these factors expressions, thereby being an effective therapeutic agent for a cancer.

1.7. Plasma-Induced Oxidative Stress

Cellular reactive oxygen species (ROS) formed in cells may eventually induce cell death. In this regard, it was determined whether ROS is effectively induced in plasma-treated HNSCC cells as well, and whether this induces MUL1-mediated AKT degradation, using N-acetyl cysteine (NAC), an anti-oxidant substance. The result is shown in FIG. 8.

As shown in FIG. 8, AKT and p-AKT levels induced by plasma were prevented by NAC pretreatment. Also, NAC inhibited plasma-induced binding between AKT and MUL1 in PLA assays. The result demonstrates that the plasma-induced ROS system plays a pivotal role in MUL1-mediated AKT ubiquitination in HNSCC cells.

Example 2. Head and Neck Cancer Cell Death by Liquid Type Plasma (LTP)

2.1 Preparation of Liquid Type Plasma (LTP)

As confirmed above, although plasma has an excellent treatment effect for head and neck cancer, it is inconvenient in delivery for in vivo applications. In order to improve this disadvantage, liquid type plasma (LIP) was prepared as a novel substance having an anticancer effect equivalent to plasma. Specifically, as shown in FIG. 9, LIP was prepared with plasma-conditioned medium (PCM), obtained by irradiating, with plasma, serum-free media under various conditions varying the irradiation distance from the serum-free media and treatment time. In order to prepare optimal LIP, the concentration of ozone, ultraviolet A (UV-A), and ultraviolet B (UV-B) were measured in each LIP under different conditions, varying the distance of NTP treatment from 1 to 8 cm. For a control group, air-conditioned medium, to which plasma was not treated, was prepared to be used as control media (CM). The pH of CM or LIP does not change.

The amounts of UV-A and UV-B detected according to the distance of NTP treatment are as shown in the following Table 1.

TABLE 1

| Distance | UV A (315~400 nm) | UV B (280~315 nm) |
| --- | --- | --- |
| 1 cm | 337 mW/cm$^2$ | 156 mW/cm$^2$ |
| 2 cm | 144 mW/cm$^2$ | 49 mW/cm$^2$ |
| 3 cm | 98 mW/cm$^2$ | 31 mW/cm$^2$ |
| 4 cm | 80 mW/cm$^2$ | 19 mW/cm$^2$ |
| 5 cm | 47 mW/cm$^2$ | 15 mW/cm$^2$ |
| 6 cm | 40 mW/cm$^2$ | 12 mW/cm$^2$ |
| 7 cm | 30 mW/cm$^2$ | 9 mW/cm$^2$ |
| 8 cm | 27 mW/cm$^2$ | 7 mW/cm$^2$ |

As shown in Table 1, at the distance of 1 to 2 cm, UV-A and UV-B, which are known as having an anticancer effect, were remarkably highly generated.

Further, the ROS concentration was detected using CHE-Metrics® Kit (Midland, Va., USA) in the prepared LIP. Five LIP samples were prepared per each ROS-detection assay. The ozone concentration was measured using a Colorimeter. The five differently prepared LIP samples were combined into one sample, and each concentration was measured according to the kit manual. As shown in Table 2, it was confirmed that NTP treatment for 15 minutes leads to very high amounts of ROS and ozone which have an anticancer effect.

TABLE 2

| ROS | Concentration (ppm ± SD) |
| --- | --- |
| Ozone ($O_3$) | 1.154 ± 0.00145 |
| Hydrogen ($H_2O_2$) | 1.8333 ± 0.3152 |
| Oxygen ($O_2$) | 4.767 ± 0.1453 |
| Nitrate (No) | 0.1673 ± 0.1663 |

Data are expressed as means ± SD.

Based on the above result, finally, LIP with an optimal anticancer effect was prepared with 15 ml of culture media under the conditions of irradiating the media with NTP at a distance of 1 to 2 cm from the media for 15 minutes. After measuring the pH, the prepared LIP was applied to anticancer effect tests.

2.2 Cancer Cell Viability by LTP Treatment

In order to determine whether LIP shows the same plasma treatment effect on head and neck cancer cells as described above, after treating head and neck cancer cells with LIP, changes in AKT, p-AKT, and MUL1, viability of head and neck cancer cells, and colony-forming ability of head and neck cancer cells were examined. SCC15 cells, human head and neck cancer cell line originating from oral cavity cancer, were seeded on 48-well plates, and LIP was treated thereto under free-serum conditions for 24 hours. After 24 hours, cell viability was measured using an MTT assay (n=6). For a control group, CM prepared in Example 2.1 was used. The result is shown in FIG. 10.

As shown in FIG. 10, in all of human head and neck cancer cell lines SCC15 and SCC-QLL1, cancer cell viability was reduced by the LIP treatment. Accordingly, it was confirmed that the prepared LIP has an effect of killing cancer cells, like NIP.

2.3. Confirmation on Inhibition of Colony-Forming Ability by LTP Treatment

In order to determine whether LIP inhibits colony formation of cancer cells from head and neck cancer, SCC-QLL1 cells (1000 cells) were seeded on 6-well plates. LIP containing 10% serum was replaced every other day for 2 weeks. The colony was fixed with cold methanol at room temperature for 10 minutes and stained with a crystal violet solution. The colony size was measured using the Image J program. The result is shown in FIG. 11.

As shown in FIG. 11, in LIP-treated SCC-QLL1 cells, the colony formation was significantly inhibited, as compared with the CM-treated control group.

2.4 Change in AKT, p-AKT, and MUL1 Levels by LTP Treatment

SCC15 cells were treated with LIP, and each protein expression of AKT, p-AKT, and MUL1 was evaluated by Western blot. Also, LIP was treated with scrambled RNAs or MUL1 siRNA-transfected cells for 24 hours, and LIP-induced MUL1-mediated AKT degradation was examined. CM which is not treated with NTP was used as a control group. Each protein expression was evaluated by Western blot. MUL1-mediated AKT ubiquitination was induced by LIP. In order to confirm MUL1-mediated AKT ubiquitination, SCC15 cells were transfected with MUL1 siRNA, active AKT (Myr AKT-Myc/His) and ubiquitin (Ubi-HA) plasmids.

FIGS. 12, 13, and 14 show the results of confirming changes in AKT, p-AKT, and MUL1 expression levels by the LIP treatment.

As shown in FIG. 12, LIP decreased AKT and p-AKT levels and increased MUL1 level. In contrast, CM did not change AKT, p-AKT, or MUL1 levels. The reduction of AKT and p-AKT levels induced by LIP was successfully suppressed by MUL1 knockdown through MUL1 siRNA.

Further, as shown in FIG. 13, LIP strongly induced AKT ubiquitination. Also, LIP-induced AKT ubiquitination was significantly suppressed in SCC15 cells transfected with MUL1 siRNA, as can be confirmed from FIG. 13, lines 3 to 6.

Moreover, as shown in FIG. 14, MUL1 knockdown through MUL1 siRNA inhibited LIP-induced cytotoxicity in addition to inhibition of AKT ubiquitination, thereby reducing cancer cell death by LIP.

This result demonstrates that a novel liquid type plasma prepared by being exposed to plasma has a head and neck cancer cell death accelerating effect and an anticancer effect through MUL1-mediated AKT ubiquitination, equivalent to plasma.

2.5. Treatment Effect for Head and Neck Cancer by LTP Treatment

From the above examples, it was confirmed that LIP prepared by being exposed to plasma can have an effect of suppressing a cancer through the same mechanism as plasma. Thus, specifically, in order to determine whether LIP has the same anticancer effect in vivo, cell viability, AKT degradation, or colony-forming ability was examined in two types of mouse tumor models. The colony-forming ability was evaluated by crystal violet staining and quantified. The result was expressed as means±standard deviation. First, SCC7 mouse HNC cells (1×106 cells) were administered subcutaneously in C3H/Hej mice and treated with LTP for one week.

The results are shown in FIGS. 15 and 16.

As shown in FIG. 15, as compared with the CM-treated control group, in the LTP-treated group, not only HNC cells in SCC7 cells but also AKT or p-AKT level was reduced. Rat's MUL1 was increased by LTP, but endogenous MUL1 was also detected. The colony-forming ability of SCC was strongly suppressed by LTP. FIG. 15(a) shows a result of confirming a change in SCC7 cell viability in syngeneic mouse models by LTP treatment, through an MTT assay. FIG. 15(b) shows a result of confirming changes in p-AKT, AKT, and MUL1 expressions, through Western blot. FIG. 15(c) shows a result of confirming colony-forming ability through crystal violet staining (p<0.05).

Based on the above result, SCC7 cells were administered to C3H/HeJ mice and they were treated with LTP for one week. Thereafter, changes in tumor volume, image, and weight were checked. The result is shown in FIG. 16.

As shown in FIG. 16, after 4 times treatment with LTP, the LTP-treated group was compared with the control group to confirm that tumor volume was significantly reduced and the tumor development was strongly inhibited. Also, after the final treatment with LTP, the final image and weight of tumor were significantly reduced in the LTP-treated group as compared with the control CM-treated group.

Further, to confirm the LTP's anticancer effect in xenograft in vivo models, human SCC15 HNC cells (2×106 cells) were subcutaneously inoculated into BALB/c nu/nu mouse models and treated with LTP for 10 days. In the xenograft models, LTP was administered 10 times due to gradual formation of SCC15 cells with tumor compared with syngeneic models. FIG. 17 shows the result of observing tumor volume, size, and weight after LTP administration.

As shown in FIG. 17, significant inhibition in tumor volume was detected after the ninth treatment with LTP. Further, as a result of examining the size and weight of the final tumor, inhibition on tumor size was observed with naked eyes, and significant reduction in tumor weight was also observed, as compared with the control group.

Changes in ATK, p-AKT, and MUL1 by the LTP treatment were confirmed through Western blot and immunohistochemistry analysis. The result is shown in FIG. 18.

As shown in FIG. 18, in the LTP-treated group, p-AKT level was significantly inhibited, and MUL1 level was increased by the LTP treatment, as compared with the control group. Similar to in vivo result from the syngeneic models, total AKT level did not change by the LTP treatment in the xenograft models. According to the immunohistochemistry analysis, MUL1 expression was increased in the LTP-treated tumor. p-AKT was strongly stained in the control group; however, p-AKT-positive staining was reduced by the LTP treatment. The result demonstrates that the exposure to LIP, as well as to NTP, provides an anticancer effect, and that the treatment with LTP prepared by being exposed to plasma, as well as with NTP, provides an anticancer effect the same as plasma, which is induced through the same mechanism as NTP. Accordingly, plasma and LTP prepared by treating plasma can be used as a novel therapeutic agent for a cancer.

What is claimed is:

1. An anticancer agent comprising a liquid type plasma prepared by a method comprising:
   1) filling a plasma generator with a carrier gas;
   2) generating a plasma by supplying a voltage of 0.5 kV to 20 kV to the carrier gas; and
   3) irradiating a medium with the generated plasma.

2. A method for treating a cancer, the method comprising:
   1) filling a plasma generator with a carrier gas;
   2) generating a plasma by supplying a voltage of 0.5 kV to 20 kV to the carrier gas;
   3) obtaining a liquid type plasma by irradiating a medium with the generated plasma; and
   4) treating a subject with the liquid type plasma.

3. The method of claim 2, wherein the cancer is at least one selected from the group consisting of thyroid cancer, oral cavity cancer, pharynx cancer, liver cancer, lung cancer, melanoma, and head and neck cancer.

4. The method of claim 2, wherein the carrier gas is selected from helium, oxygen or a combination thereof.

5. The method of claim 2, wherein the treatment is a treatment after a cancer operation.

* * * * *